US010561528B2

(12) United States Patent
Mazzone et al.

(10) Patent No.: US 10,561,528 B2
(45) Date of Patent: Feb. 18, 2020

(54) FLUID-CIRCULATING CATHETERS USEABLE FOR ENDOVASCULAR HEAT EXCHANGE

(71) Applicant: ZOLL Circulation, Inc., San Jose, CA (US)

(72) Inventors: James D Mazzone, San Jose, CA (US); Masoumeh Mafi, Mountain View, CA (US); Alex L Lim, Daly City, CA (US); Jack I Irwin, Campbell, CA (US); Dung A Nguyen, San Jose, CA (US)

(73) Assignee: Zoll Circulation, Inc., San Jose, CA (US)

( * ) Notice: Subject to any disclaimer, the term of this patent is extended or adjusted under 35 U.S.C. 154(b) by 310 days.

(21) Appl. No.: 15/395,858

(22) Filed: Dec. 30, 2016

(65) Prior Publication Data

US 2018/0185192 A1    Jul. 5, 2018

(51) Int. Cl.
*A61F 7/12* (2006.01)
*A61M 25/00* (2006.01)
*A61F 7/00* (2006.01)

(52) U.S. Cl.
CPC ........... *A61F 7/12* (2013.01); *A61M 25/0026* (2013.01); *A61M 25/0043* (2013.01); *A61F 2007/0056* (2013.01); *A61F 2007/126* (2013.01); *A61M 2205/3606* (2013.01)

(58) Field of Classification Search
CPC combination set(s) only.
See application file for complete search history.

(56) References Cited

U.S. PATENT DOCUMENTS

| 4,111,209 A | 9/1978 | Wolvek et al. |
| 4,259,276 A | 3/1981 | Rawlings |
| 4,298,006 A | 11/1981 | Parks |
| 4,911,232 A | 3/1990 | Colvin et al. |
| 5,837,003 A | 11/1998 | Ginsburg |
| 5,931,848 A | 8/1999 | Saadat |
| 6,019,783 A | 2/2000 | Philips et al. |
| 6,126,684 A | 10/2000 | Gobin et al. |
| 6,146,411 A | 11/2000 | Noda et al. |
| 6,149,677 A | 11/2000 | Dobak, III |
| 6,299,599 B1 | 10/2001 | Pham et al. |
| 6,301,904 B1 | 10/2001 | Goldstein |
| 6,338,727 B1 | 1/2002 | Noda et al. |
| 6,368,304 B1 | 4/2002 | Aliberto et al. |
| 6,451,045 B1 | 9/2002 | Walker et al. |
| 6,551,349 B2 | 4/2003 | Lasheras et al. |
| 6,554,797 B1 | 4/2003 | Worthen |

(Continued)

FOREIGN PATENT DOCUMENTS

| WO | WO99/52455 A1 | 10/1999 |
| WO | WO99/66970 A1 | 12/1999 |

(Continued)

OTHER PUBLICATIONS

PCT International Search Report dated Mar. 29, 2018 in related PCT Application No. US2017/069107.

*Primary Examiner* — Joseph A Stoklosa
*Assistant Examiner* — Adam J Avigan
(74) *Attorney, Agent, or Firm* — Fish & Richardson P.C.

(57) ABSTRACT

Disclosure includes fluid-circulating heat exchange catheters, systems and related methods useable for controlling a patient's body temperature.

22 Claims, 7 Drawing Sheets

(56) References Cited

U.S. PATENT DOCUMENTS

| | | |
|---|---|---|
| 6,581,403 B2 | 6/2003 | Whitebrook |
| 6,585,692 B1 | 7/2003 | Worthen |
| 6,589,271 B1 | 7/2003 | Tzeng et al. |
| 6,592,612 B1 | 7/2003 | Samson et al. |
| 6,610,083 B2 | 8/2003 | Keller et al. |
| 6,673,042 B1 | 1/2004 | Samson et al. |
| 6,679,907 B2 | 1/2004 | Dobak et al. |
| 6,695,873 B2 | 2/2004 | Dobak et al. |
| 6,703,127 B2 | 3/2004 | Davis et al. |
| 6,706,060 B2 | 3/2004 | Tzeng et al. |
| 6,749,625 B2 | 6/2004 | Pompa et al. |
| 6,796,995 B2 | 9/2004 | Pham et al. |
| 6,835,334 B2 | 12/2004 | Davis et al. |
| 6,881,551 B2 | 4/2005 | Heller et al. |
| 7,255,709 B2 | 8/2007 | Walker et al. |
| 7,287,398 B2 | 10/2007 | Noda et al. |
| 7,389,653 B2 | 6/2008 | Kasza et al. |
| 7,566,341 B2 | 7/2009 | Keller et al. |
| 7,857,781 B2 | 12/2010 | Noda et al. |
| 7,963,986 B2 | 6/2011 | Machold et al. |
| 8,911,485 B2 | 12/2014 | Brian, III et al. |
| 9,278,023 B2 | 3/2016 | Dabrowiak |
| 9,314,367 B2 | 4/2016 | Callister et al. |
| 9,492,633 B2 | 11/2016 | Dabrowiak |
| 2001/0007951 A1 | 7/2001 | Dobak, III |
| 2001/0016764 A1 | 8/2001 | Dobak |
| 2002/0045925 A1 | 4/2002 | Keller et al. |
| 2002/0116039 A1* | 8/2002 | Walker ............... A61F 7/12 607/105 |
| 2002/0183816 A1 | 12/2002 | Tzeng et al. |
| 2002/0193738 A1 | 12/2002 | Adzich et al. |
| 2003/0222378 A1 | 12/2003 | King et al. |
| 2004/0044387 A1 | 3/2004 | Pompa et al. |
| 2004/0050154 A1 | 3/2004 | Machold et al. |
| 2004/0076826 A1 | 4/2004 | Lee |
| 2004/0106969 A1 | 6/2004 | Dobak, III et al. |
| 2004/0111138 A1 | 6/2004 | Bleam et al. |
| 2005/0010273 A1 | 1/2005 | Walker et al. |
| 2005/0076924 A1 | 4/2005 | Dobak, III |
| 2005/0240250 A1 | 10/2005 | Dobak, III |
| 2006/0161232 A1 | 7/2006 | Kasza et al. |
| 2007/0043409 A1 | 2/2007 | Brian, III et al. |
| 2007/0191810 A1 | 8/2007 | Kennedy |
| 2007/0207186 A1 | 9/2007 | Scanlon et al. |
| 2008/0071337 A1 | 3/2008 | Dobak, III et al. |
| 2008/0193653 A1 | 8/2008 | Oh |
| 2009/0043366 A1 | 2/2009 | Dae |
| 2009/0125087 A1 | 5/2009 | Becker et al. |
| 2009/0234325 A1 | 9/2009 | Rozenberg et al. |
| 2009/0247963 A1 | 10/2009 | Bleam |
| 2009/0255276 A1 | 10/2009 | Kasza et al. |
| 2010/0036473 A1 | 2/2010 | Roth |
| 2010/0324635 A1 | 12/2010 | Kreck |
| 2011/0022136 A1 | 1/2011 | Scott |
| 2011/0088413 A1 | 4/2011 | Lampe |
| 2011/0106051 A1 | 5/2011 | Saab |
| 2011/0152680 A1 | 6/2011 | Kim et al. |
| 2013/0079855 A1 | 3/2013 | Helkowski et al. |
| 2013/0090708 A1 | 4/2013 | Dabrowiak et al. |
| 2013/0178923 A1* | 7/2013 | Dabrowiak ............... A61F 7/12 607/105 |
| 2015/0230975 A1 | 8/2015 | Dabrowiak et al. |

FOREIGN PATENT DOCUMENTS

| | | |
|---|---|---|
| WO | WO00/32126 A1 | 6/2000 |
| WO | WO2009/117586 A2 | 9/2009 |

* cited by examiner

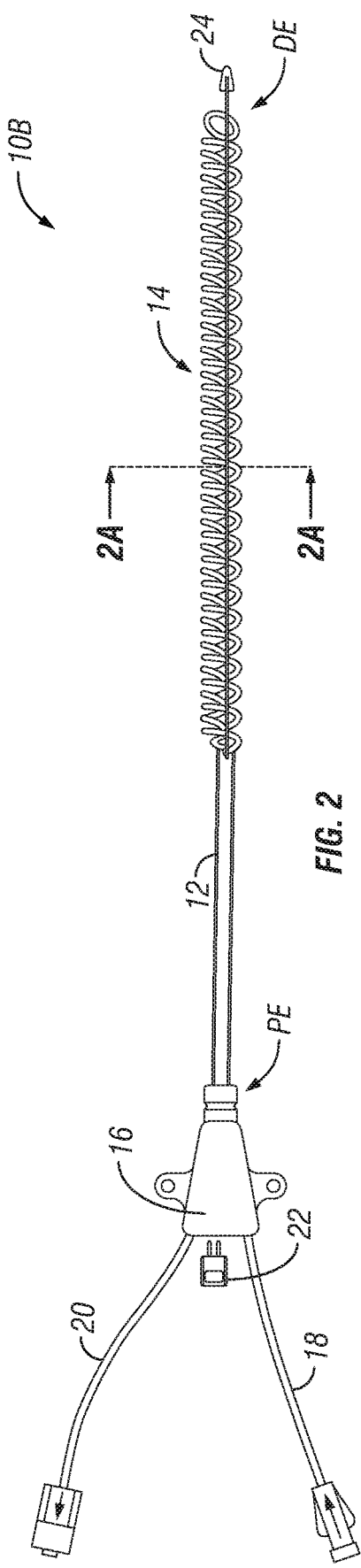
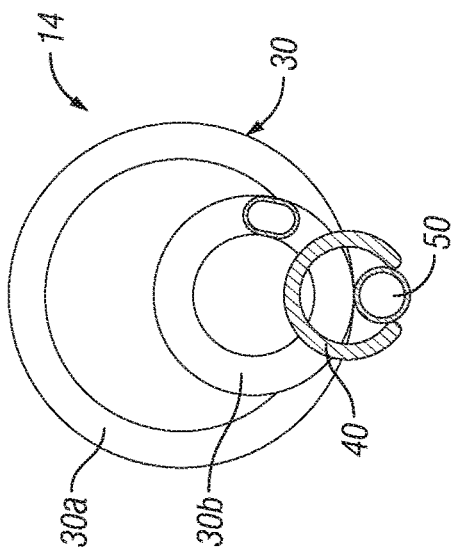
FIG. 2
FIG. 2A

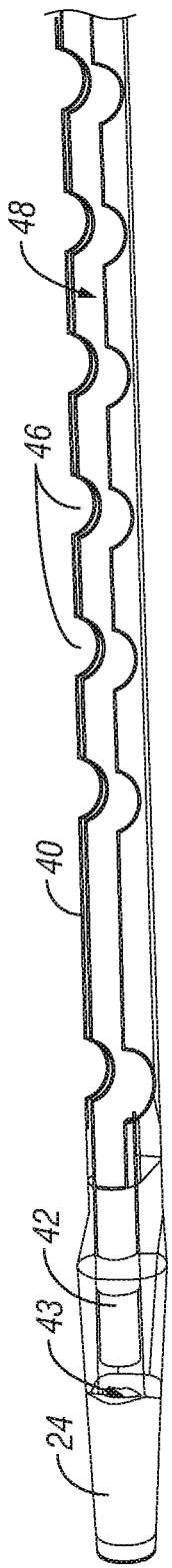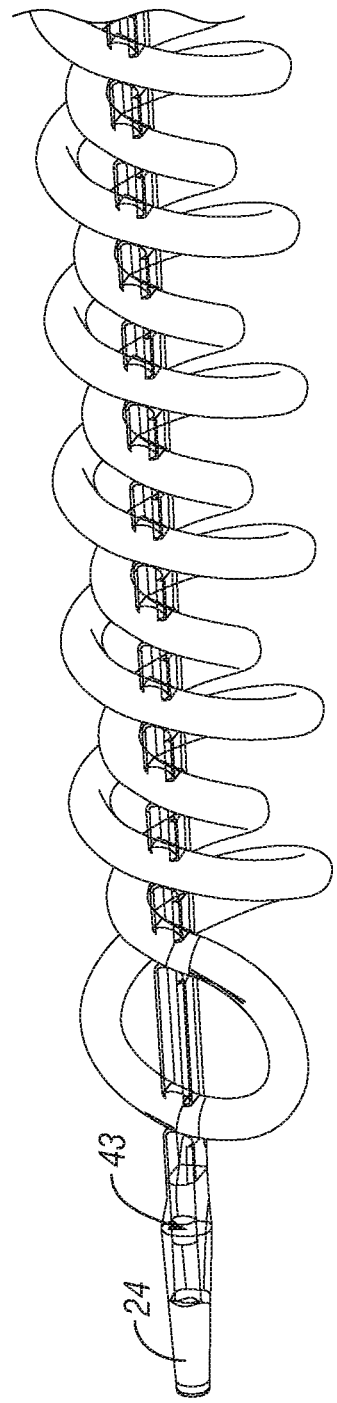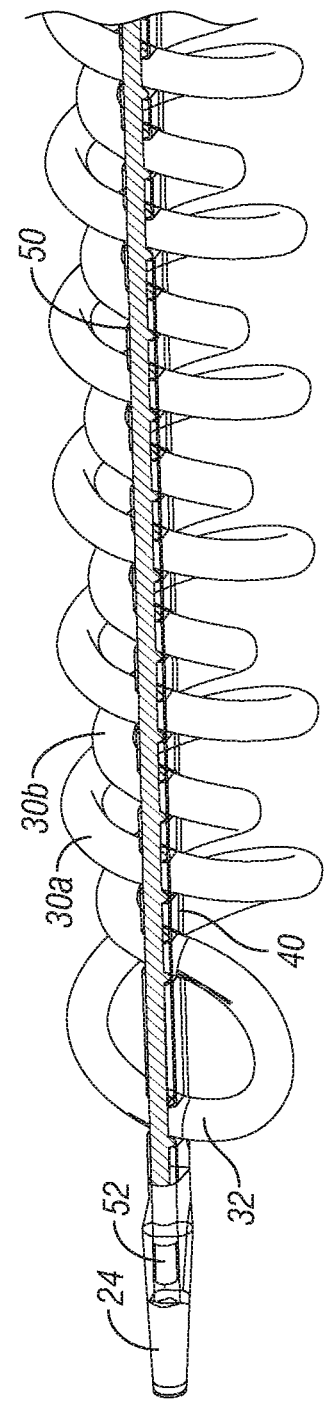

FLUID-CIRCULATING CATHETERS USEABLE FOR ENDOVASCULAR HEAT EXCHANGE

FIELD OF THE INVENTION

The present disclosure relates generally to the fields of medicine and engineering and more particularly to fluid-circulating catheters useable for controlling a patient's body temperature by endovascular heat exchange and related methods.

BACKGROUND

Pursuant to 37 CFR 1.71(e), this patent document contains material which is subject to copyright protection and the owner of this patent document reserves all copyright rights whatsoever.

In modern medicine there are numerous clinical situations in which it is desirable to control or modify body temperature of a patient. For example, hypothermia can be induced in humans and some animals for the purpose of protecting various organs and tissues against the effects of ischemic, anoxic or toxic insult. For example, hypothermia can have neuroprotective and/or cardioprotective effects in patients who suffer an ischemic event such as a myocardial infraction or acute coronary syndrome, post-anoxic coma following cardiopulmonary resuscitation, traumatic brain injury, stroke, subarachnoid hemorrhage, fever or neurological injury. Also, studies have shown that hypothermia can ameliorate nephrotoxic effects of radiographic contrast media (e.g., radiocontrast nephropathy) in patients who have pre-existing renal impairment.

One method for inducing hypothermia—or otherwise modifying or controlling a patient's body temperature—involves insertion of an endovascular heat exchange catheter into the patient's vasculature and circulation of a heat exchange fluid, such as warmed or cooled saline solution, through a heat exchanger located on the catheter. This results in exchange of heat between the circulating heat exchange fluid and blood that is coursing through the patient's vasculature. Because the blood circulates throughout the patient's entire body, this technique can be effective to change the patient's core body temperature to a desired target temperature and to thereafter maintain the target core body temperature for a period of time.

In some clinical situations, it is desirable to induce hypothermia as rapidly as possible. Once such example is in the treatment of acute myocardial infarction. Patients who are diagnosed with acute myocardial infarction are often treated with a coronary intervention or surgery (e.g., angioplasty or coronary artery bypass surgery) to reperfuse the ischemic myocardium. In at least one study, it was observed that patients with anterior wall infarctions whose core body temperature had been lowered to at least 35° C. prior to reperfusion by angioplasty had significantly smaller median infarct size than other patients with anterior wall infarctions whose core body temperature was greater than 35° C. at the time of reperfusion. This observation is not explained by other factors such as time-to-presentation, lesion location or quantity of antegrade coronary flow (TIMI Flow) prior to the angioplasty. This would suggest that, at least in acute myocardial infarction cases, it is desirable to lower the patient's body temperature to at least 35° C. as rapidly as practical so that reperfusion may also be accomplished as rapidly as practical after such hypothermia has been induced.

SUMMARY

In accordance with the present disclosure, described herein are heat exchange catheter devices, systems and methods which are useable for efficient endovascular heat exchange.

In many cases, the time required to raise or lower a patient's body temperature using an endovascular heat exchange catheter is dependent to at least some degree on the heat heat-exchanging efficiency of the heat exchange catheter. The present disclosure describes improved heat exchange catheters, systems and methods which provide high-efficiency heat exchange and the ability to rapidly raise or lower a patient's body temperature.

In accordance with one embodiment, there is provided a catheter device which comprises: a catheter body having a distal end, a first lumen and a second lumen; a spine or other elongate member which extends distally from the catheter body, such spine or other elongate member having a plurality of spaced-apart heat exchange member-receiving features therein or thereon. At least one heat exchange member (e.g., one or more heat exchange tubes) is disposed on the spine or other elongate member and connected to the first and second lumens such that fluid may circulate in a distal direction through the first lumen, then through said at least one heat exchange member, then in a proximal direction through the second lumen.

In accordance with another embodiment there is provided a catheter device which comprises: a catheter body having a distal end, a first lumen and a second lumen; a spine or other elongate member which differs from the catheter body and extends distally from the catheter body and at least one heat exchange member (e.g., one or more heat exchange tubes) disposed on the spine or elongate member and connected to said first and second lumens of the catheter body such that fluid may circulate in a distal direction through the first lumen, then through said at least one heat exchange member and then in a proximal direction through the second lumen.

In accordance with yet another embodiment, there is provided a catheter device which comprises: a catheter body having a distal end, a first lumen and a second lumen; an elongate member attached to the catheter body and extending beyond the distal end of the catheter body; at least one tube disposed on said elongate member and connected to said first and second lumens such that fluid may circulate in a distal direction through the first lumen, then through said at least one tube and then in a proximal direction through the second lumen; and an elongate luminal member attached to the catheter body and extending substantially parallel to the elongate member, said elongate luminal member having a through lumen extending therethrough; wherein the elongate member comprises tube-receiving features which correspond to the size and shape of elongate member-contacting locations on said at least one tube, the elongate member-contacting locations on said at least one tube are positioned in the tube-receiving features of the elongate member, and the elongate luminal member extends along the elongate member so as to hold the elongate member-contacting locations of said at least one tube in the tube-receiving locations of the elongate member.

In accordance with yet another embodiment, there is provided a method of manufacturing a catheter comprising the steps of: forming or obtaining a proximal catheter body having a distal end and at least first and second lumens extending therethrough; forming or obtaining a spine or other elongate member; disposing at least one tube on the spine or other elongate member; attaching the spine or other elongate member to the proximal catheter body such that the spine or other elongate member extends beyond the distal end of the catheter body; connecting said at least one tube to at least the first and second lumens such that fluid will flow in a distal direction through the first lumen, then through said at least one tube, and then in a proximal direction through the second lumen.

In accordance with still another embodiment, there is provided a method for imparting a desired curved or looped shape to a tube or other workpiece which has a lumen or passageway extending therethrough. This method generally comprises the steps of i) advancing the tube or other workpiece over or in the forming member while the forming member is in an initial (e.g., substantially straight) configuration; ii) causing the forming member to transition to the desired curved or looped shape, thereby imparting that curved or looped shape to the tube or other workpiece positioned on the forming member; and removing the forming member from the tube or other workpiece while maintaining the tube or other workpiece in the desired curved or looped configuration. This method may be used to impart the looped configuration to heat exchange tubes or other luminal heat exchange members used on various catheter described herein.

In accordance with other embodiments, there are provided systems which comprise any catheter described herein in combination with fluid pumping apparatus operative to cause fluid to circulate in a distal direction through at least one heat exchange member (or at least one segment of a unitary heat exchange member) and then return in a proximal direction through a second heat exchange member (or second segment of a unitary heat exchange member). Such systems may include additional components such as fluid heating or cooling and control apparatus. Examples of endovascular heat exchange systems having pumping, heating/cooling and control apparatus useable in conjunction with the present catheters include but are not limited to those described in U.S. Pat. No. 8,911,485 (Brian III, et al.); U.S. Pat. No. 9,314,367 (Callister, et al.) and U.S. Pat. No. 9,278,023 (Dabrowiak) as well as United States Patent Application Publication No. 2015/0230975 (Dabrowiak et al.), the entire disclosure of each such patent and application being expressly incorporated herein by reference. Additionally incorporated herein by reference are the entire disclosure of U.S. Pat. No. 9,492,633 (Dabrowiak) and the entire disclosures of U.S. patent application Ser. No. 13/631,076 (US PG Pub. 2013/0178923) and Ser. No. 13/631,324 (US PG Pub. 2013/0090708).

In accordance with other embodiments, there are provided methods for modifying or controlling body temperature of a human or animal subject wherein the method comprises the steps of: (i) inserting any embodiment of a catheter described herein into vasculature of the subject such and (ii) circulating heated or cooled heat exchange fluid through the catheter to thereby exchange heat with the subject's flowing blood resulting in modification or control of the subject's body temperature, to treat various conditions, e.g., to treat acute myocardial infarction.

In accordance with yet another embodiment, there is provided a recirculating distal tip for a circulating fluid catheter in which a fluid circulates in a distal direction through a first member on the catheter and then returns in the proximal direction through a second member on the catheter. The recirculating distal tip member has a hollow inner cavity and is connected to the first and second member such that fluid which flows in the distal direction through the first member will pass through the hollow inner cavity of the recirculation tip member and then into the second member such that it will then flow in the proximal direction through the second member. In some embodiments, the catheter may have a through lumen tube which extends through the hollow inner cavity of the recirculating distal tip to an opening in the distal end of the recirculating tip member. The through lumen tube is sealed to the recirculating distal tip member such that fluid which circulates through the hollow inner cavity of the recirculating tip member will not leak into or enter the lumen of the through lumen tube and any fluid that is infused through the trough lumen tube will not leak into or enter the hollow inner cavity of the recirculating tip member.

Still further aspects and details of the present invention will be understood upon reading of the detailed description and examples set forth herebelow.

BRIEF DESCRIPTION OF THE DRAWINGS

The following detailed description and examples are provided for the purpose of non-exhaustively describing some, but not necessarily all, examples or embodiments of the inventions described herein, and shall not limit the scope of the inventions in any way.

FIG. 2 is a side view of one embodiment of an endovascular heat exchange catheter.

FIG. 2A is a cross-sectional view through line 2A-2A of FIG. 2.

FIG. 3A is a side view of the elongate member, FIG. 3B is a side view of the heat exchange tube and FIG. 3C is a side view of an optional elongate luminal member and the distal tip member.

FIGS. 4A through 4C show certain steps in a process which may be used for assembling the distal portion of the endovascular heat exchange balloon catheter embodiment of FIG. 2. Specifically, FIG. 4A shows the elongate member with the distal tip member mounted thereon; FIG. 4B shows the heat exchange tube mounted on the elongate member and FIG. 4C shows the optional elongate luminal member mounted on the elongate member along with the heat exchange tube.

DETAILED DESCRIPTION

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

Applicant is filing on even date herewith a patent application entitled High Efficiency Heat Exchange Catheters for Control of Patient Body Temperature, the entire disclosure of which is expressly incorporated herein by reference.

Figure 1:
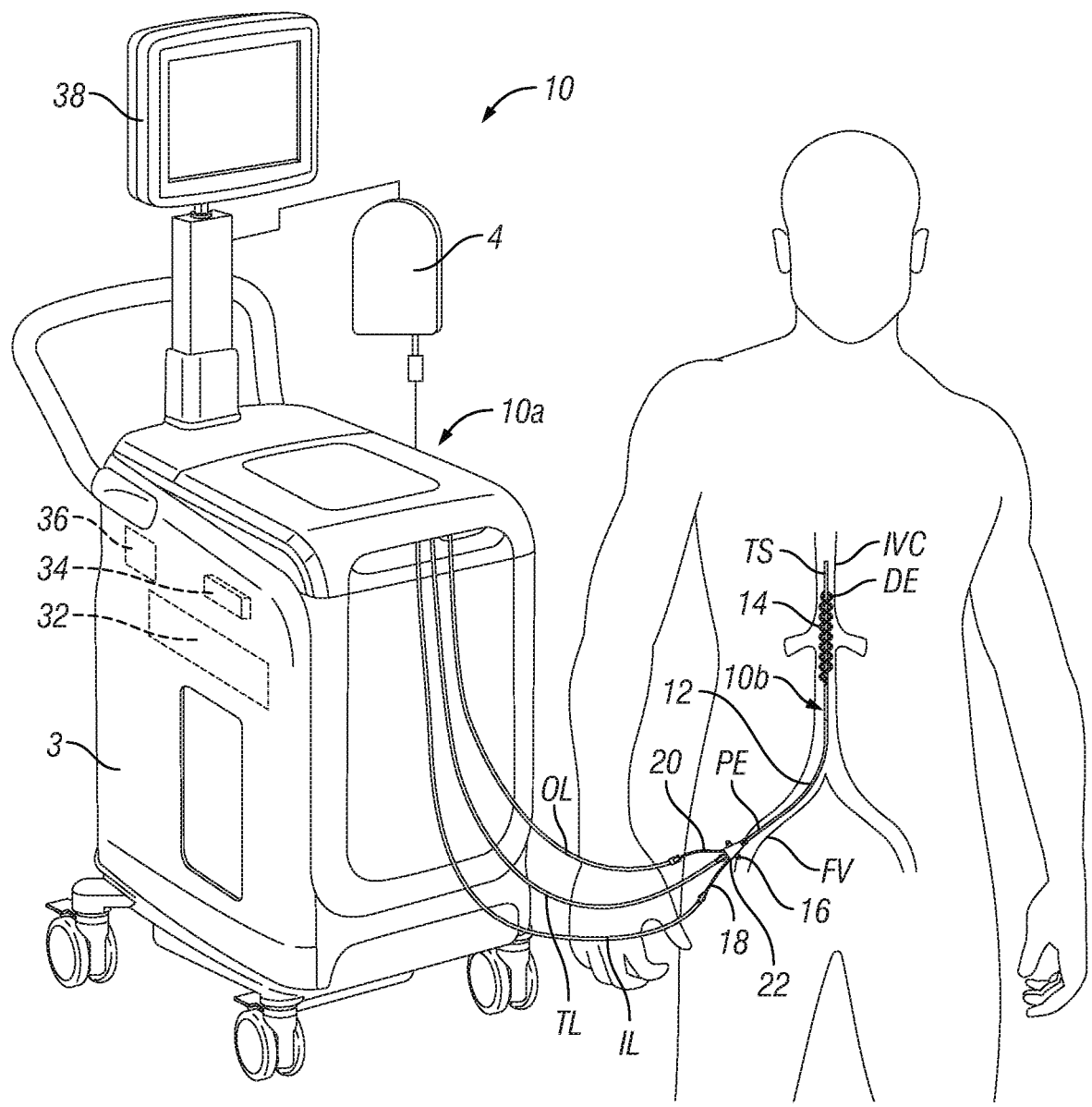
FIG. 1 shows an endovascular temperature management system which includes an endovascular heat exchange catheter.

FIG. 1 shows an endovascular temperature management system 10 which generally includes a control console 10a and an endovascular heat exchange catheter 10b. FIGS. 2 and 2A show further details of the endovascular heat exchange catheter 10b.

The console 10a comprises a housing 3 within which, or on which, there are positioned heating/cooling apparatus 32 for alternately heating and cooling a heat exchange fluid, a pump 34 for pumping the heat exchange fluid and a programmable controller 36. A user interface 38, such as a liquid crystal display (LCD), is in communication with the controller 36. The user interface displays system information and also receives user input as well as sensor data, as described more fully herein.

A source of heat exchange fluid 4, such as a bag or container of sterile 0.9% NaCl solution, is connected by tubing to the heater/cooler 32. Also connected to the heater/cooler 32 are proximal ends of a heat exchange fluid outflow line OL and a heat exchange fluid inflow line IL.

A body temperature sensor TS is connected by way of a temperature lead TL, or alternatively by wireless connectivity, to the controller 36.

The endovascular heat exchange catheter 10b generally comprises a proximal catheter body 12 and an endovascular heat exchange assembly 14. In this particular embodiment, the proximal catheter body 12 has three lumens, an inflow lumen, an outflow lumen and an optional through lumen. The heat exchange assembly 14 comprises a spine or elongate member 40 and at least one heat exchange member 30 disposed on the spine or elongate member 40. The heat exchange assembly 14 is attached to and extends distally from the proximal catheter body 12, as shown. An introducer sheath may be used to introduce the catheter into a patient's body. Alternatively, the catheter may be introduced without using an introducer sheath.

Figure 3A:
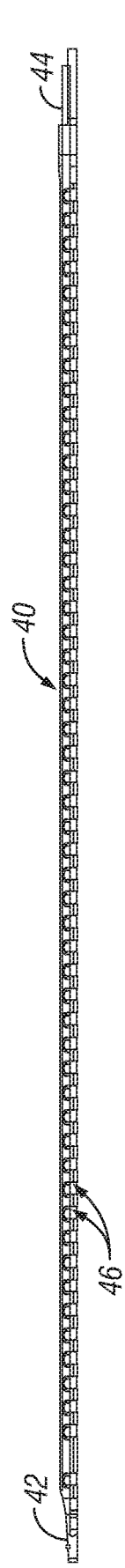
FIGS. 3A through 3C show certain components of the endovascular heat exchange catheter embodiment of FIG. 2. Specifically.

The term "elongate member," may mean, in at least some embodiments, a member, e.g., a spine or similar structure, which extends from a catheter body and upon which at least one heat exchange member is disposed. In at least some embodiments, the elongate member 40 is distinguishable from the catheter body 12 on the basis of one or more differences in structure or physical property. For example, the elongate member 40 may be more or less rigid than the catheter body. Also for example, the elongate member 40 may have receiving features 46 configured to receive the heat exchange member(s) 30. Such receiving features 46 may comprise transverse notches formed in one side of the elongate member as seen in FIGS. 3A and 4A or, alternatively, may comprise any other clips, clamps, cradles, projections, prongs, depressions, indentations, locator marks, notches, grooves, troughs, apertures, bores, through-holes or open areas in or on which the heat exchange member(s) 30 may be fully or partially positioned. In some embodiments, the elongate member 40 may be formed of solid or substantially solid material and/or may be devoid of any lumen(s) that extend longitudinally through the elongate member 40. In some embodiments, the elongate member 40 may have one or more lumens extending longitudinally through the elongate member 40. Alternatively, in certain embodiments, the elongate member may comprise a continuation, e.g., a distal portion, of the catheter body, with receiving features formed on one or more sides thereof. Wherein such receiving features include, e.g., clips, clamps, cradles, projections, prongs, depressions, indentations, notches, grooves, troughs, etc.

In the particular embodiment shown, the elongate member 40 comprises an elongate, generally C-shaped member having receiving features 46 which comprise spaced-apart transverse notches, recesses or grooves formed along the open side of the generally C-shaped member, as may be appreciated from FIGS. 3A and 4A. The heat exchange member(s) 30 may be inserted in these recessed, groove, or notch-type receiving features 46 such that the helical loops extend around the closed side of the generally C-shaped elongate member 40. The heat exchange member(s) 30 may be secured to the receiving features 46 by adhesive or other suitable means. Additionally, or alternatively, one or more member(s) may be secured along the open side or within the channels formed by the generally C-shaped elongate member 40 so as to capture and retain the heat exchange member(s) 30 within the recessed, groove, or notch-type receiving features 46. For example, an elongate luminal member 50, such as a plastic tube, may be affixed to the elongate member 40 along its open side after insertion of the heat exchange member(s) 30 into the receiving features 46, thereby capturing the heat exchange member(s) 30 within the receiving features 46 and affixing or securing the heat exchange member(s) 30 to the elongate member 40. This may be appreciated from FIGS. 2A and 4C. The dimensions of the receiving features can vary to accommodate heat exchange members of various sizes to maximize heat exchange performance and optimize catheter profile. The dimensions of the elongate member, including its open side can vary to accommodate elongate luminal members or through lumens having various sizes to optimize catheter profile. Alternatively, any elongate member may be a shape other than generally C-shaped. In certain embodiments, the open side of the elongate member may be closed, such that it is not C-shaped, but instead includes a series of openings or enclosed channels through which an elongate luminal member may be threaded or inserted.

As explained more fully below, the lumen of the optional elongate luminal member 50 may serve as a through lumen of the catheter 10b useable for guidewire passage, infusion of medicaments or fluids, insertion of the temperature sensor TS or other functions.

In certain embodiments, the elongate member 40 may be molded, notched, or extruded. In certain embodiments, the elongate member 40 may be attached to the proximal catheter body 12 by any suitable means. In this example, a proximal extension 44 of the elongate member 40 is inserted into the distal end of the proximal catheter body 12 and secured therein by adhesive, clamp or fastener and/or tied or fastened to the catheter body with a plastic tubing, string or other tying mechanism or material (e.g., PET or other type of polymer). The heat exchange member(s) 30 may comprise first and second helical, spiral or curved heat exchange segments 30a and 30b formed of noncompliant polymeric material, such as polyethylene terephthalate (PET), Pebax, Polyolefin, Polyurethane and/or Nylon or other suitable compliant or noncompliant material. Segments 30a and 30b may have outer diameters of about 16.6 mm and 11 mm, respectively, and wall thicknesses of about 0.0127 mm. However, suitable diameters and thicknesses may vary. For example, the diameter of either heat exchange segment may be in the range of 2 mm-19 mm and the thickness can be in the range of 0.0006 mm-0.1 mm. In certain embodiments a heat exchange segment may be formed of polymer material having a diameter of 0.095" and a wall thickness of 0.0005", when empty, the heat exchange segment may be collapsible to a size that will pass through a 12 French or greater introducer, and/or when filled with fluid, the heat exchange segment may assume an expanded configuration having a diameter in the range of from approximately 0.600 inch to approximately 0.700 inch.

The proximal end of the first segment 30a is connected to the inflow lumen of the catheter body 12. The proximal end of the second segment 30b is connected to the outflow lumen of the catheter body 12. The heat exchange member(s) 30 may comprise a single continuous heat exchange tube. Alternatively, the heat exchange member(s) 30 may comprise one or more heat exchange tubes. For example, heat exchange segments 30a and 30b may be separate heat exchange tubes, the distal ends of which may be connected to each other by a connection, e.g., a connection tube, lumen or other connecting element.

Figure 5A:
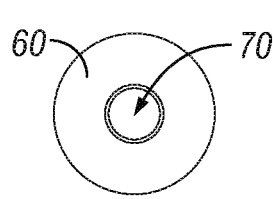
FIG. 5A is a distal end view of the recirculating distal tip member of FIG. 5.
Figure 5:
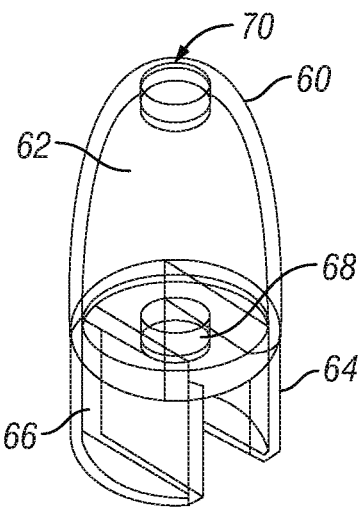
FIG. 5 is a perspective view of one embodiment of a recirculating distal tip member which may be used on any of the endovascular heat exchange catheters described herein.
Figure 5B:
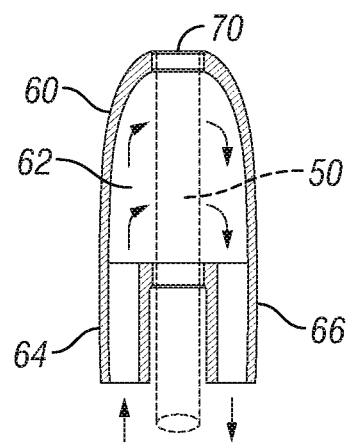
FIG. 5B is a longitudinal sectional view of the recirculating distal tip member of FIG. 5 with the optional elongate luminal member (shown in dotted lines) inserted therethrough.

The first and second heat exchange segments 30a and 30b of heat exchange member 30 are disposed on the elongate member 40 such that heat exchange fluid will circulate from the inflow lumen of the catheter body 12, in the distal direction through the first heat exchange segment 30a, then in the proximal direction through the second heat exchange segment 30b and into the outflow lumen of the catheter body 12. Alternatively, in other embodiments, heat exchange member 30 may be connected to a recirculating tip member through which the heat exchange fluid will circulate from the first segment 30a into the second segment 30b, via the recirculating tip member. One example of such a recirculating distal tip member 60 is shown in FIGS. 5 through 5B and discussed more fully below. Alternatively, in still other embodiments, the distal end of separate heat exchange tubes 30a, 30b may be connected to a recirculating tip member through which the heat exchange fluid will circulate from the first tube 30a into the second tube 30b.

In the non-limiting example shown in FIGS. 1 through 3C, the first heat exchange segment 30a (or the first heat exchange tube if formed of two or more separate heat exchange tubes) has equidistantly spaced helical loops of a first fully-inflated diameter and the second heat exchange segment 30b (or the second heat exchange tube if formed of two or more separate heat exchange tubes) has equidistantly spaced helical loops of a second fully-inflated diameter. The second fully inflated diameter is smaller than the first fully inflated diameter. In other embodiments, the first fully-inflated diameter may be smaller than the second fully-inflated diameter, or the first and second fully-inflated diameters may be equal in size.

The number and diameter(s) of the loops may vary depending on various factors, such as the size of the patient's body, the size of the blood vessel in which the catheter is to be inserted and the heat exchange power required for the intended procedure. In the non-limiting example seen in FIGS. 2 and 3B, the heat exchange member has a total of 54 loops, the larger loops in the first heat exchange segment 30a has a fully inflated diameter of 16.6 mm and the smaller loops of the second heat exchange segment 30b has a fully inflated diameter of 11 mm. Also, in this example, loops of the heat exchange segments 30a, 30b are positioned within receiving features 46 on the elongate member 40. Such positioning causes the loops to be aligned equidistantly or substantially equidistantly in a single row with the large loops of the first heat exchange segment 30a alternating with the smaller loops of the second heat exchange segment 30b. The receiving features 46 of the elongate member 40 may be specifically located in the elongate member to guide proper placement of each loop during manufacture, thereby ensuring that the loops are placed in their intended positions with the intended spacing between adjacent loops. In certain embodiments, the number of loops may range from 44 to 54 loops. A hub 16 is mounted on the proximal end PE of the proximal catheter body 12. The hub 16 has an inflow connector 18 that is connected to the inflow lumen of the catheter body 12, an outflow connector 20 that is connected to the outflow lumen of the proximal catheter body 12 and a through lumen connector 22 that is connected to the optional through lumen of the proximal catheter body 12.

An inflow line IL extends from the heater/cooler 32 to the catheter's inflow connector 18. An outflow line OL extends from the catheter's outflow connector 20 to the heater cooler 32. One or more temperature leads TL with temperature sensor(s) TS may be positioned in any suitable location(s) on or in the subject's body for sensing of the intended body temperature(s). A temperature lead TL having one or more temperature sensor(s) TS may be inserted through the lumen connector 22 and through the catheter 10b. The temperature lead TL serves to connect the temperature sensor(s) TS to the controller 36. Alternatively wireless connectivity may be used instead of the temperature lead TL. In some embodiments, the temperature sensor TS need not be inserted through the catheter 10a as shown in FIG. 1 but, rather, one or more body temperature sensor(s) TS may be positioned at any other suitable location on or in the subject's body to provide real time feedback of the subject's current body temperature to the controller 36. In some embodiments, a temperature sensor TS may be inserted through a catheter and a second TS may be positioned at any other suitable location on or in the subject's body.

Figure 3B:
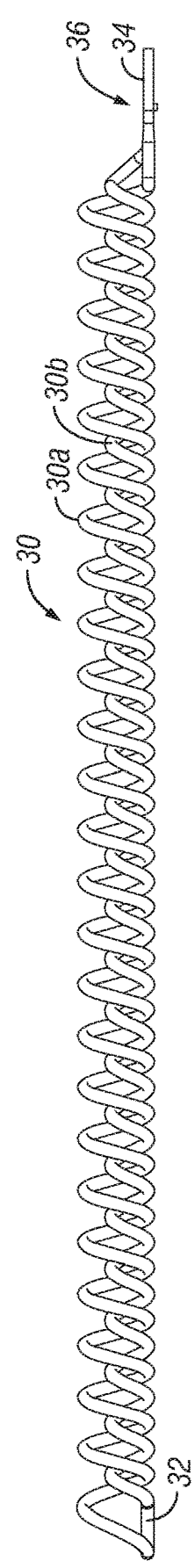
Figure 3C:
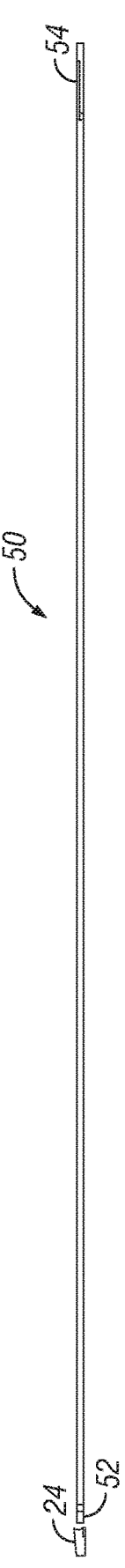

FIGS. 3A through 3C show an exploded view of certain components of the endovascular heat exchange assembly 14 of catheter 10b. Specifically, FIG. 3A is a side view of the elongate member 40. FIG. 3B is a side view of a heat exchange member 30 which comprises the first heat exchange segment 30a and second heat exchange segment 30b described above. FIG. 3C is a side view of an optional elongate luminal member 50 and an optional distal tip member 24.

FIGS. 4A through 4C show certain steps in a process which may be used for assembling the heat exchange assembly 14 of catheter 10b. After the heat exchange member(s) has been set in the looped configuration, elongate member-contacting locations on the loops are inserted in the receiving features 46 of the elongate member 40, as shown in FIG. 4B. Adhesive may be applied to secure each loop within each receiving feature 46. Thereafter, if the optional elongate luminal member 50 is to be used, the distal end 52 of the elongate luminal member 50 is inserted into a distal structure 42 of the elongate member 40 such that the lumen of the elongate luminal member 50 is aligned with an optional bore that extends longitudinally through a distal tip member 24, which may optionally be attached to the distal end of the elongate member 40, as shown in detail in FIG. 4A. The length of the elongate luminal member 50 is then snapped into, mounted on and/or affixed, by adhesive, clamp or fastener and/or tied or fastened with a plastic tubing, string or other tying mechanism or material (e.g., PET or other type of polymer) to the open side of the generally C-shaped elongate member 40, as seen in FIG. 4C as well as the cross sectional view of FIG. 2A.

After the heat exchange assembly 14 has been assembled, the proximal ends of the heat exchange member(s) 30 is/are inserted into and secured to the inflow and outflow lumens of the proximal catheter body 12. Also, if present, the proximal end 52 of the optional elongate luminal member 50 is inserted into and secured to the optional through lumen of the proximal catheter body 12. Additionally, the proximal extension 44 of the elongate member 40 is inserted into and secured to the proximal catheter body 12.

FIGS. 5 though 5B show one embodiment of an optional recirculating tip member 60 which may be used on certain embodiments of heat exchange catheter described herein, or other types of recirculating fluid catheters. This recirculating distal tip member 60 comprises a generally bullet-shaped or blunt-tipped cylindrical structure having a hollow inner cavity 62. An inflow connector 64 and outflow connector 66 are formed on the proximal end of the recirculating tip member 60. When this recirculating distal tip member 60 is mounted on the end of the above-described catheter 10b, the distal end of heat exchange tube 30a will not be directly connected by way of connector 32 to the distal end of heat exchange tube 30b. Rather, the distal end of heat exchange tube 30a will be connected to inflow connector 64 and the distal end of heat exchange tube 30b will be connected to outflow connector 66. In this manner, heat exchange fluid will flow out of the distal end of heat exchange tube 30a, through inflow connector 64, through the hollow inner cavity 62 of the distal tip member 60, through outflow connector 66 and into the distal end of heat exchange tube 30b. In catheters which include the optional elongate luminal member 50, the recirculating tip member 60 will have optional proximal and distal openings 68, 70. A distal portion or extension of the elongate luminal member 50 will be inserted through proximal opening 68, advanced through inner cavity 62 and sealed to the distal opening 70, as seen in FIG. 5B. In this manner, the lumen of the elongate luminal member 50 is fluidly isolated from the inner cavity 62 of the distal tip member 60 such that heat exchange fluid may circulate through the inner cavity 62 and around the outer surface of the elongate luminal member 50 without entering or leaking into the lumen of the elongate luminal member 50. The recirculating tip member 60 may be of multi-piece or single piece construction any may be formed of any suitable material, including radiopaque materials. Examples of materials of which the recirculating tip member 60 may be formed include aluminum, 90%/10% platinum-iridium, and/or ceramic. In certain embodiments, a lumen may extend from proximal opening 68, through inner cavity 62, to distal opening 70, providing a lumen through which an elongate luminal member may extend, which lumen is fluidly isolated from the inner cavity 62 of the distal tip member 60 such that heat exchange fluid may circulate through the inner cavity 62 and around the outer surface of the lumen without entering or leaking into the lumen.

Figure 6:
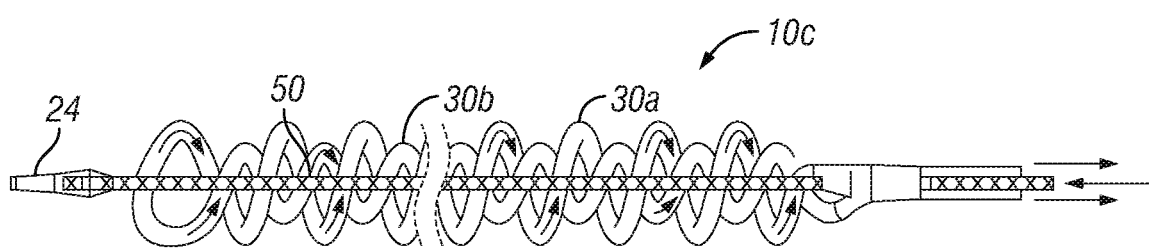
FIG. 6 is a side view of a distal portion of an alternative embodiment of an endovascular heat exchange catheter.

FIG. 6 shows an alternative embodiment of a heat exchange catheter 10c. In this embodiment, the lumen of the elongate luminal member 50 terminates proximal to the distal end of the catheter and is connected to the distal ends of the heat exchange tubes 30a, 30b. As indicated by arrows, heat exchange fluid may be circulated in the distal direction through the lumen of elongate luminal member 50 and then in the proximal directions through both of the heat exchange tubes 30a and 30b. This effectively results in distally-directed inflow of heat exchange through a single straight lumen followed by outflow (return) of the heat exchange fluid through both of the looped heat exchanged tubes. The elongate luminal member may be insulated to minimize heat gain or loss as the cooled or warmed heat exchange fluid is being delivered to the distal ends of the heat exchange tubes 30a, 30b. Although this example shows a single inflow lumen with two looped outflow lumens, it is to be appreciated that any number of inflow and outflow lumens may be employed. Optionally, the elongate luminal member may have one or a plurality of lumens. For example, one or more lumens may serve as a through lumen useable for guidewire passage, infusion of medicaments or fluids, insertion of the temperature sensor TS or other functions.

Alternatively, with reference to FIG. 6, the flow directions may be inverted such that heat exchange fluid circulates in the distal direction through the looped heat exchange tubes 30a, 30b and then returns in the proximal direction through the lumen of the elongate luminal member 50. Optionally, any of the heat exchange catheter embodiments described herein may include a recirculating tip member 60.

Figure 7:
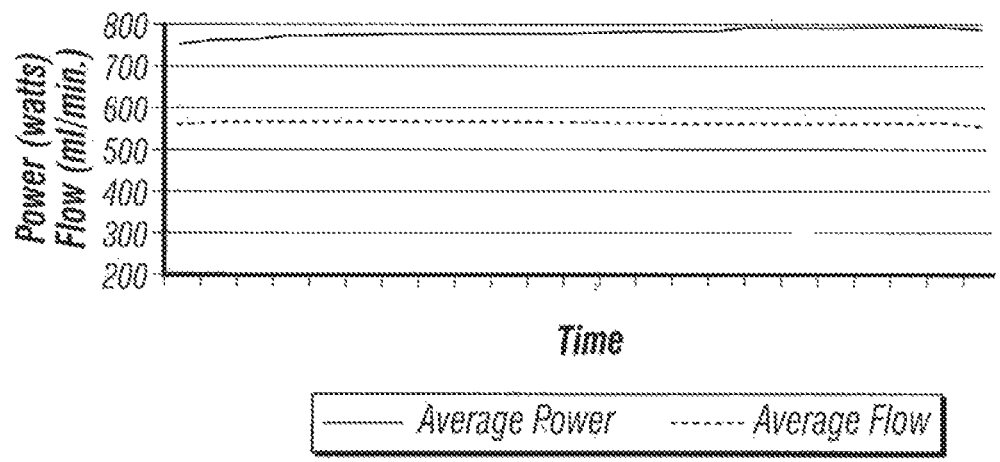
FIG. 7 is a graph of power and flow versus time in an endovascular heat exchange catheter embodiment of the type shown in FIG. 2 wherein heat exchange fluid is pumped in the distal direction through a first looped heat exchange tube and returns in the proximal direction through a second looped heat exchange tube.
Figure 8:
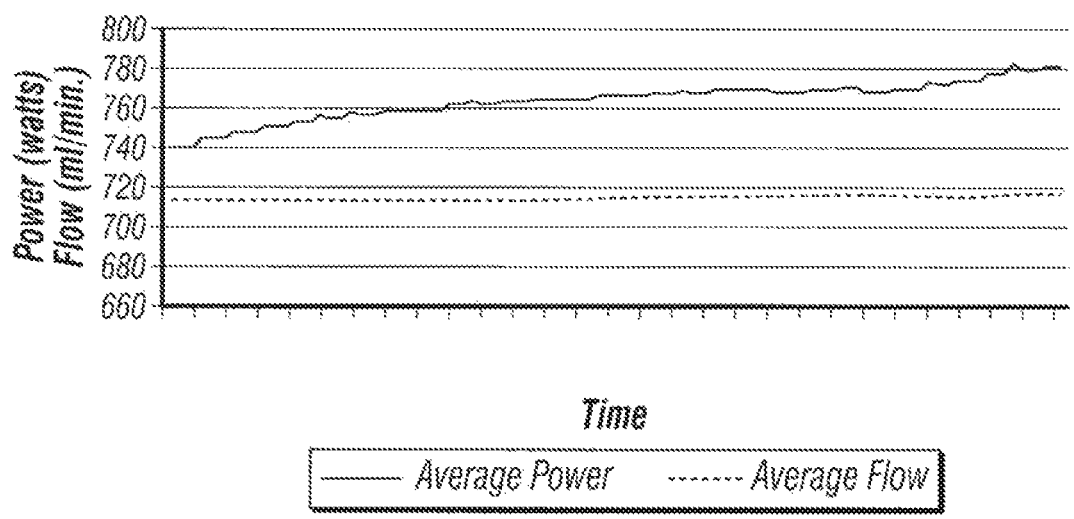
FIG. 8 is a graph of power and flow versus time in an alternative endovascular heat exchange catheter embodiment of the type shown in FIG. 6, wherein heat exchange fluid is pumped in the distal direction through a straight inflow lumen and then returns in the proximal direction through both of the looped heat exchange tubes.
Figure 9:
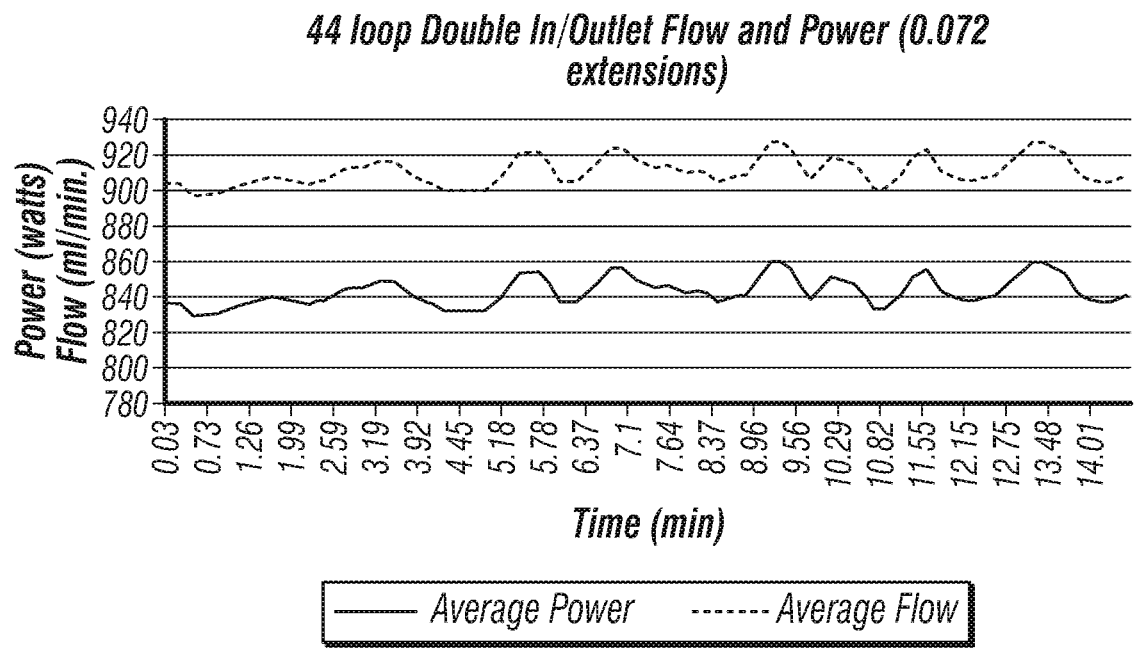
FIG. 9 is a graph of power and flow versus time in an alternative endovascular heat exchange catheter embodiment of the type shown in FIG. 6, wherein the heat exchange fluid is pumped in the distal direction through both of the looped heat exchange tubes and then returns in the proximal direction through a single, straight return lumen.

The number and configuration of inflow and outflow lumens used will affect flow rate of the heat exchange fluid and heat exchange power of the catheter. FIGS. 7 through 9 show graphic representations of catheter power and flow rate vs. time for several different catheter configurations of the present disclosure in an experimental bench top model representing IVC flow and temperature for the purpose of measuring heat exchange. In this water based model, a catheter is placed in a cylinder up to the manifold (16). 37° C. water is circulated at a rate of 2.5 L/min in the cylinder in the direction of manifold (16) to balloon (14). Two thermistors are attached to the catheter. One to the outlet (20) and one to the inlet (18) luers. A console that is able to provide 60 psi of pressure and saline at ≤4° C. fluid is connected to the catheter's luers. On the outlet side of the catheter flow a flow meter is installed. FIG. 7 shows power and flow versus time for the first embodiment of a heat exchange catheter 10b as shown in FIG. 2, wherein the heat exchange member 30 has a total of 54 loops and wherein heat exchange fluid is pumped in the distal direction through the first heat exchange segment 30a wherein the larger loops are formed and returns in the proximal direction through the second heat exchange segment 30b wherein the smaller loops are formed.

Flow rate is measured by a flow meter positioned at the outlet of the catheter. Power is calculated by the following formula: Power=0.0697 ($\Delta$T*Flow), where temperature T is in Celsius and Flow is in ml/min.

As seen in FIG. 7, the first embodiment of the catheter 10b consistently provides power between 750 and 800 Watts at a substantially constant flow rate of approximately 580 ml/min.

FIG. 8 is a graph of power and flow versus time in an alternative embodiment of an endovascular heat exchange catheter 10c of the type shown in FIG. 6, wherein the looped heat exchange tubes 30a, 30b have a total of 44 loops and wherein the heat exchange fluid is circulated in the distal direction through the lumen of the elongate luminal member 50 and then returns in the proximal direction through both of the looped heat exchange tubes 30a, 30b.

As seen in FIG. 8, this embodiment provides power which increases gradually from approximately 740 Watts to approximately 780 Watts at a substantially constant flow rate of approximately 715-720 ml/min.

FIG. 9 is a graph of power and flow versus time in an alternative embodiment of an endovascular heat exchange catheter 10c of the type shown in FIG. 6, wherein the looped heat exchange tubes 30a, 30b have a total of about 44 loops, and wherein the heat exchange fluid is circulated in the distal direction through both of the looped heat exchange tubes 30a, 30b and returns in the proximal direction through the lumen of the elongate luminal member 50. In other embodiments, the number of loops may be from 20 to 60.

As seen in FIG. 9, this embodiment provides catheter power which varies between approximately 900 Watts and approximately 925 Watts at flow rats which vary between approximately 830 ml/min and approximately 860 ml/min.

Figure 10:
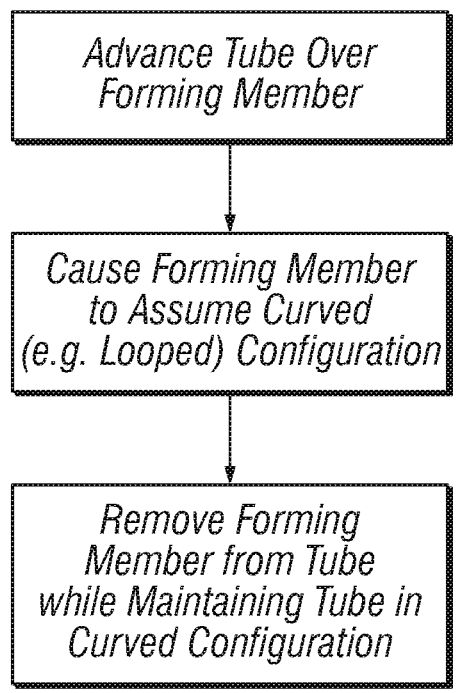
FIG. 10 is a flow diagram showing steps in a method for creating tubes having curved (e.g., looped) configurations

FIG. 10 is a flow diagram which shows steps in an exemplary method for forming the desired loops in the heat exchange member 30. In this method, a shape memory forming member, such as a segment of nickel titanium (Nitinol) wire, is used to impart the desired looped configuration to the heat exchange member 30 or any other tube or workpiece having a lumen that extends therethrough. Initially, the heat exchange member, tube or other workpiece in which loops are to be created is advanced over the forming member while the forming member is in a non-looped (e.g., substantially straight) initial configuration. Thereafter, the forming member is caused to transition from its initial configuration to the desired looped configuration, thereby also causing the heat exchange member, tube or other workpiece to assume such looped configuration. Thereafter, the forming member is removed from the heat exchange member, tube or other workpiece while the member, tube or other workpiece is maintained in the looped configuration. In this manner, loops of the desired number, size, shape and spacing may be formed in the heat exchange member 30 and/or tubes 30a and 30b or other tube or luminal workpieces. In some embodiments, the forming member may be formed of a shape memory nickel-titanium alloy or other material and the step of causing the forming member to transition from its first configuration to the desired second configuration may be accomplished by changing the temperature of the forming member to cause the forming member to transition from the first shape to the second shape. For applications where the method is used to induce the desired looped configuration to the heat exchange member 30 or tubes 30a, 30b of catheters of the present disclosure, the forming member may comprise a nickel-titanium alloy wire formed of e.g., Nitinol that is 50/50 by weight of Titanium and Nickle having a shape memory transition temperature of about 4-10 degrees C. or below 20 degrees and/or above 35 degrees. In an alternative embodiment, the shape memory forming member may be in the form of a tube. The tube has a lumen in which the heat exchange member would be inserted. This tube shape memory forming member would transition between a straight and looped configuration, thereby imparting the desired looped configuration in the heat exchange member.

The heat exchange catheters described herein provide a number of advantages over existing heat exchange catheters. For example, the elongate member or spine 40 may provide the rigidity or column strength necessary to advance the heat exchange assembly 14 to the intended location within the subject's vasculature. The elongate member 40 may make it easier to manufacture the catheter 10b, compared to tying the balloon around an extended guidewire lumen or other member. The elongate member may be injected molded with teeth/grooves or other receiving features for receiving the heat exchange member, tube or balloon which hold each loop of a heat exchange member, tube or balloon in place, and maintain spacing between the loops. This may be especially advantageous when working with a heat exchange member, tube or balloon having looped supply and return lumens with many loops. The elongate member 40 may allow the heat exchange assembly 14 to have a relatively small cross sectional profile when deflated (e.g., 2 to 16 French or 10 to 14 French or 12 French. Also, the receiving features 46 of the elongate member 40 maintain spacing of the loops, thereby making the heat exchange member(s) 30 less obstructive within the vessel. This may allow for better blood flow through and around the balloon and decrease the risk of blood clot formation compared to a more obtrusive catheter construction in which the heat exchange member(s) are wrapped around a catheter body or adjacent loops of a heat exchange member are not evenly spaced apart. The heat exchange catheters, systems and methods described herein may provide high-efficiency heat exchange and the ability to rapidly raise or lower a patient's body temperature.

It is to be appreciated that, although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the absence or substantial absence of any other element, step, member, component, composition, reactant, part or portion unless otherwise noted. All reasonable additions, deletions, modifications and alterations are to be considered equivalents of the described examples and embodiments and are to be included within the scope of the following claims.

What is claimed is:

1. A catheter device comprising:
 a catheter body having a distal end, a first lumen and a second lumen;
 an elongate member which extends distally from the catheter body, said elongate member having a plurality of spaced-apart heat exchange member-receiving features therein or thereon;

at least one heat exchange member disposed on the elongate member and connected to said first and second lumens such that fluid may circulate in a distal direction through the first lumen, then through said at least one heat exchange member, then in a proximal direction through the second lumen;

a third lumen extending through the catheter body; and an elongate luminal member attached to the catheter body and extending substantially parallel to the elongate member, said elongate luminal member which has a lumen extending longitudinally therethrough;

wherein portions of said at least one heat exchange member are captured between the elongate member and the elongate luminal member.

2. A catheter device according to claim 1 wherein said at least one heat exchange member comprises at least one tube configured in a series of loops.

3. A catheter device according to claim 2 wherein the loops are helical.

4. A catheter device according to claim 3 wherein helical loops of a first size are formed in a first tube or first tube segment helical loops of a second size are formed in a second tube or second tube segment.

5. A catheter device according to claim 1 wherein said at least one heat exchange member comprises a continuous tube having a first segment which runs from the catheter body to a distal location on the elongate member and a second segment that returns from the distal location on the elongate member to the catheter body.

6. A catheter device according to claim 1 wherein said at least one heat exchange member is selected from:
  a single heat member having a first segment through which heat exchange fluid circulates in a distal direction and a second segment through which heat exchange fluid circulates in a proximal direction;
  a plurality of heat exchange members including at least a first heat exchange member through which heat exchange fluid circulates in a distal direction and a second heat exchange member which is connected to the first heat exchange member such that fluid which has flowed in the distal direction through the first heat exchange member then flows in the proximal direction through the second heat exchange member.

7. A catheter device according to claim 6 wherein the at least one heat exchange member comprises a first heat exchange member through which heat exchange fluid circulates in a distal direction, a second heat exchange member through which heat exchange fluid circulates in a proximal direction and a fluidic connection between the first and second heat exchange members, and, wherein:
  the fluidic connection comprises a recirculating distal tip on a distal end of the elongate member, wherein the first and second heat exchange members are connected to the recirculating distal tip such that fluid may flow from the first lumen of the catheter body, in a distal direction through the first heat exchange member, through the recirculating distal tip, in a proximal direction through the second heat exchange member and then into the second lumen of the catheter body.

8. A catheter device according to claim 1 wherein helical loops of a first size are formed in a first heat exchange member segment or first heat exchange member and helical loops of a second size are formed in a second heat exchange member segment or second heat exchange member.

9. A catheter device according to claim 1 wherein:
  the elongate member has receiving features formed therein or thereon, said receiving features corresponding to the size and shape of elongate member-contacting locations on said at least one heat exchange member; and
  the elongate member-contacting locations on said at least one heat exchange member are positioned in the receiving features.

10. A catheter device according to claim 9 wherein the receiving features are selected from: clips, projections, prongs, depressions, indentations, locator markings, notches, grooves, troughs, apertures, bores, through holes and open areas formed in the elongate member within which said locations on said at least one heat exchange member is/are fully or partially positioned.

11. A catheter device according to claim 1 wherein said at least one heat exchange member has between 44 and 54 helical loops.

12. A catheter device comprising:
  a catheter body having a distal end, a first lumen and a second lumen;
  an elongate member which extends distally from the catheter body, said elongate member having a plurality of spaced-apart heat exchange member-receiving features therein or thereon;
  at least one heat exchange member disposed on the elongate member and connected to said first and second lumens such that fluid may circulate in a distal direction through the first lumen, then through said at least one heat exchange member, then in a proximal direction through the second lumen;
  a third lumen extending through the catheter body; and
  an elongate luminal member attached to the catheter body and extending substantially parallel to the elongate member, said elongate luminal member having a lumen extending longitudinally therethrough;
  wherein:
    the elongate member comprises an elongate member having receiving features formed thereon or therein, said receiving features corresponding to the size and shape of elongate member-contacting locations on said at least one heat exchange member,
    the elongate member-contacting locations on said at least one heat exchange member are positioned in the receiving features formed on or in the elongate member; and
    the elongate luminal member is mounted on the elongate member so as to retain said at least one heat exchange member within the receiving features.

13. A catheter device according to claim 12 wherein:
  a series of said receiving features are formed along the elongate member;
  said at least one heat exchange member is formed in a series of loops,
  elongate member-contacting locations on at least some of the loops are positioned in the receiving features; and,
  the elongate luminal member is mounted on the elongate member so as to retain said loops within the receiving features.

14. A catheter device according to claim 13 wherein said at least one heat exchange member is also adhered to the elongate member.

15. A catheter device according to claim 13 wherein helical loops are formed in said at least one heat exchange member and wherein the helical loops are arranged to alternate between loops of a first diameter and loops of a second diameter.

16. A catheter device according to claim 15 wherein the size and number of helical loops is such that the catheter is capable of delivering at least about 600 watts of cooling power when saline solution operated within a rigid 22 mm ID tube through which water at a temperature of 37 degrees C. is pumped at a rate of 2.5 liters per minute.

17. A catheter device comprising:

a catheter body having a distal end, a plurality of inflow lumens and a single outflow lumen;

an elongate member which extends distally from the catheter body, said elongate member having a plurality of spaced-apart heat exchange member-receiving features therein or thereon;

at least one heat exchange member disposed on the elongate member and connected to said plurality of inflow lumens and said single outflow lumen such that fluid may circulate in a distal direction through the plurality of inflow lumens, then through said at least one heat exchange member, then in a proximal direction through said single outflow lumen;

a through lumen extending through the catheter body; and an elongate luminal member attached to the catheter body and extending substantially parallel to the elongate member, said elongate luminal member having a lumen extending longitudinally therethrough;

wherein portions of said at least one heat exchange member are captured between the elongate member and the elongate luminal member; and a plurality of distal circulation tubes or tube segments, each of which is connected to an inflow lumen of the catheter body and a single proximal circulation tube or tube segment which is connected to the outflow lumen of the catheter body;

wherein fluid may be circulated in the distal direction through the plurality of inflow lumens, then in the distal direction through the plurality of distal circulation tubes or tube segments, then in the proximal direction through the single proximal circulation tube or tube segment and then in the proximal direction through the single outflow lumen of the catheter body.

18. A catheter device comprising:

a catheter body having a distal end, a single inflow lumen and a plurality of outflow lumens;

an elongate member which extends distally from the catheter body, said elongate member having a plurality of spaced-apart heat exchange member-receiving features therein or thereon;

at least one heat exchange member disposed on the elongate member and connected to said single inflow lumen and said plurality of outflow lumens such that fluid may circulate in a distal direction through the single inflow lumen, then through said at least one heat exchange member, then in a proximal direction, through the plurality of outflow lumens;

a through lumen extending through the catheter body; and an elongate luminal member attached to the catheter body and extending substantially parallel to the elongate member, said elongate luminal member having a lumen extending longitudinally therethrough;

wherein portions of said at least one heat exchange member are captured between the elongate member and the elongate luminal member; and wherein said heat exchange member comprises:

a single distal circulation tube or tube segment which is connected to the inflow lumen of the catheter body and a plurality of proximal circulation tubes or tube segments, each of which is connected to an outflow lumen of the catheter body;

wherein fluid may be circulated in the distal direction through the single inflow lumen, then in the distal direction through the single distal circulation tube or tube segment, then in the proximal direction through the plurality of proximal circulation tubes or tube segments and then in the proximal direction through the plurality of outflow lumens of the catheter body.

19. A catheter device comprising:

a catheter body having a distal end, a first lumen and a second lumen;

an elongate member attached to the catheter body and extending beyond the distal end of the catheter body;

at least one tube disposed on said elongate member and connected to said first and second lumens such that fluid may circulate in a distal direction through the first lumen, then through said at least one tube and then in a proximal direction through the second lumen; and an elongate luminal member attached to the catheter body and extending substantially parallel to the elongate member, said elongate luminal member having a through lumen extending therethrough;

wherein the elongate member comprises tube-receiving features within which separate locations on said at least one tube are positioned, thereby causing said at least one tube to be disposed in a configuration on said elongate member; and wherein the tube-receiving features have openings, the locations on said at least one tube are inserted through the openings and into the tube-receiving features and the elongate tubular member is affixed to the elongate member in a manner that retains said at least one tube within the tube receiving features.

20. A catheter device according to claim 19 wherein said configuration comprise a coiled or looped configuration.

21. A catheter device according to claim 19 wherein the tube-receiving features are selected from: clips, projections, prongs, depressions, indentations, locator markings, notches, grooves, troughs, apertures, bores, through holes and open areas formed in the elongate member, within which the spaced-apart locations on said at least one tube are positioned.

22. A catheter device according to claim 19 wherein said at least one tube is coiled or looped such that the catheter is capable of delivering at least about 600 watts of cooling power when saline solution operated within a rigid 22 mm ID tube through which water at a temperature of 37 degrees C. is pumped at a rate of 2.5 liters per minute.

* * * * *